(12) United States Patent
Broyles et al.

(10) Patent No.: US 8,807,394 B2
(45) Date of Patent: Aug. 19, 2014

(54) SYSTEM COMPRISING A MIXING AND DISPENSING DEVICE AND A MATERIAL CONTAINER

(75) Inventors: Bruce R. Broyles, Oakdale, MN (US); Marc Peuker, Schondorf (DE); Alexander Walter, Pürgen (DE); Manfred Harre, Landsberg am Lech (DE); Karin Watzek, Kaufbeuren (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/641,741

(22) PCT Filed: Apr. 21, 2011

(86) PCT No.: PCT/US2011/033422
§ 371 (c)(1),
(2), (4) Date: Oct. 22, 2012

(87) PCT Pub. No.: WO2011/137025
PCT Pub. Date: Nov. 3, 2011

(65) Prior Publication Data
US 2013/0037570 A1    Feb. 14, 2013

(30) Foreign Application Priority Data

Apr. 29, 2010  (EP) .................................... 10161535

(51) Int. Cl.
*B67D 7/70* (2010.01)

(52) U.S. Cl.
USPC ........ 222/137; 222/145.6; 222/327; 222/333; 222/386; 433/89

(58) Field of Classification Search
USPC .................. 222/63, 94, 129, 135–137, 145.1, 222/145.5, 145.6, 325–327, 333, 386, 222/389–391; 604/208–211, 151–155, 191; 433/80, 89–90, 114–130
See application file for complete search history.

(56) References Cited

U.S. PATENT DOCUMENTS

| 3,570,719 | A | * | 3/1971 | Schiff ........................... 222/137 |
| 3,767,085 | A | * | 10/1973 | Cannon et al. .................. 222/82 |
| 5,332,122 | A | | 7/1994 | Herold |

(Continued)

FOREIGN PATENT DOCUMENTS

| DE | 3237353 | 4/1984 |
| JP | 2000201951 | 7/2000 |

OTHER PUBLICATIONS

Machine Translation of DE 3237353. DE3237353MT.pdf.*
English Language Abstract for DE 3237353 dated Apr. 12, 1984.

(Continued)

*Primary Examiner* — Paul R Durand
*Assistant Examiner* — Randall Gruby

(57) ABSTRACT

A system comprises an automatic mixing and dispensing device for a dental substance, and a material container. The mixing and dispensing device comprises a reservoir for receiving the dental substance, and first and second pressure plates. The material container has first and second material chambers for containing components of a material. The first and second material chambers have first and second cross-sectional chamber areas. At least one of the first and second cross-sectional chamber areas is smaller than smallest surface area of the first and second pressure plates. The system helps facilitating preparation and handling of dental materials.

14 Claims, 9 Drawing Sheets

(56) References Cited

U.S. PATENT DOCUMENTS

| | | | |
|---|---|---|---|
| 5,445,614 A * | 8/1995 | Haber et al. | 604/89 |
| 5,520,658 A * | 5/1996 | Holm | 604/191 |
| 5,582,596 A * | 12/1996 | Fukunaga et al. | 604/191 |
| 5,692,642 A | 12/1997 | Brattesani | |
| 5,743,431 A | 4/1998 | Brattesani | |
| 5,848,894 A * | 12/1998 | Rogers | 433/90 |
| 5,875,928 A * | 3/1999 | Muller et al. | 222/82 |
| 6,048,201 A * | 4/2000 | Zwingenberger | 433/90 |
| 6,223,936 B1 * | 5/2001 | Jeanbourquin | 222/1 |
| 6,500,001 B2 * | 12/2002 | Horth et al. | 433/89 |
| 6,716,195 B2 * | 4/2004 | Nolan et al. | 604/131 |
| 6,854,621 B2 * | 2/2005 | Keller | 222/137 |
| 2002/0170926 A1 * | 11/2002 | Horner et al. | 222/137 |
| 2004/0039368 A1 * | 2/2004 | Reilly et al. | 604/500 |
| 2004/0164097 A1 | 8/2004 | Orecchia | |
| 2007/0023450 A1 * | 2/2007 | Horth et al. | 222/137 |
| 2007/0158362 A1 * | 7/2007 | Muller-Paul | 222/137 |
| 2008/0140017 A1 * | 6/2008 | Spofforth | 604/204 |
| 2008/0144426 A1 | 6/2008 | Janssen | |
| 2008/0203112 A1 * | 8/2008 | Peuker et al. | 222/137 |

OTHER PUBLICATIONS

English Language Abstract for JP 2000201951 dated Jul. 25, 2000.
PCT Search Report for PCT/US2011/033422 mailed Jun. 29, 2011.
Extended EP Search Report for EP 10 16 1535 dated Mar. 21, 2011.

* cited by examiner

SYSTEM COMPRISING A MIXING AND DISPENSING DEVICE AND A MATERIAL CONTAINER

CROSS REFERENCE TO RELATED APPLICATIONS

This application is a national stage filing under 35 U.S.C. 371 of International Application No. PCT/US2011/033422, filed Apr. 21, 2011, which claims priority to European Application No. 10161535.9, filed Apr. 29, 2010. The disclosures of both applications are incorporated by reference in their entirety herein.

FIELD OF THE INVENTION

The invention relates to a system which comprises an automatic mixing and dispensing device for a dental substance and a material container. Further the invention relates to a use of an automatic mixing and dispensing device for a dental substance with a material container, and to an adaptor for use with the system.

BACKGROUND ART

For preparation of dental materials as needed treatments of a patient's tooth or teeth dispensing devices are available which, for example, help extruding a material from a package, or help mixing one or more components to form a mixture. In recent years motor driven devices have been developed for the preparation of dental impression materials. Such automatic devices typically allow for automatic mixing and dispensing of two-component dental impression materials. Typically dental impression materials are used at larger amounts of several centiliters per treatment, and the automatic devices are typically provided with powerful motors to mix and dispense those amounts in a relatively short time. An exemplary device for mixing and dispensing a dental impression material is for example available under the designation 3M™ ESPE™ Pentamix™ from 3M ESPE AG, Germany.

Appropriate packages for use with such devices are available on the market, which contain individual components of the material. Typically the automatic mixing and dispensing devices have pressure plates that are movable for generally simultaneously extruding the material components from such a package through a mixer in which the components are mixed prior to the mixture is made available for use at a nozzle in the mixer. Some mixing and dispensing devices are configured for dynamically mixing of the components. Appropriate mixers typically have a moving part, for example a mixing rotor, for actively agitating the components while they are supplied through the mixer.

Although there is a variety of mixing and dispensing devices on the market there is a desire for facilitating the preparation and handling of dental materials. Further the preparation and handling of dental materials should be relatively inexpensive and convenient.

SUMMARY OF THE INVENTION

In one aspect the invention relates to a system comprising an automatic mixing and dispensing device for a dental substance, and a material container. The mixing and dispensing device comprises a reservoir for receiving the dental substance. The system further comprises a first and a second pressure plate which are movable parallel to a dispensing axis. The dispensing axis preferably extends generally parallel to a direction in which the dental substance can be advanced for dispensing. The first pressure plate at or adjacent a free end has a first pressure plate surface laterally to the dispensing axis, and the first pressure plate surface has a first pressure plate area.

The term "area" for the purpose of this specification preferably refers to a surface area of a surface or a cross-sectional area of an opening which is typically measured in surface units, like for example in $mm^2$.

Further the second pressure plate at or adjacent a free end has a second pressure plate surface laterally to the dispensing axis, and the second pressure plate surface has a second pressure plate area. For example the pressure plates may be generally circular at or adjacent their free ends and may be movable in an axial direction of the circle, which is a direction parallel to the dispensing axis. The first and second pressure plate areas preferably belong to an outer, or outermost, periphery of the respective pressure plate. Further the pressure plate surfaces are typically surfaces which are used to exert a pressure on the dental substance for advancing the substance. The pressure plate surfaces in use of the mixing and dispensing device typically face the dental substance.

Further the material container of the system has a first and a second material chamber for containing components of a material. In one embodiment the first and second material chambers each contain a component of a dental material, and in particular of one of a temporary crown and bridge material or a two component composite. The components are preferably flowable components, for example liquids or pastes. In particular the components may have a relatively high viscosity within a range of 5 Pas to 100 Pas, and in more particular within a range of 10 Pas to 50 Pas. The first and second material chambers have first and second chamber cross-sections, respectively, each extending generally uniformly over a chamber length. Preferably the first and second chamber cross-sections are inner cross-sections of the chamber. The first and second chamber cross-sections have first and second chamber areas, respectively.

Further the mixing and dispensing device comprises a first plunger and a second plunger which are movable generally parallel to the dispensing axis for extruding material from the material container. The first plunger is preferably adapted to cooperate with the first material chamber, and the second plunger is preferably adapted to cooperate with the second material chamber. For example the first and second plungers may be insertable within the first and second material chambers to extrude material therefrom.

The first plunger has a free first front end oriented toward the material container. The first plunger may further have a free first rear end oriented away from the material container. The first plunger at or adjacent the first front end has a first plunger front surface laterally to the dispensing axis. The first plunger front surface has a first plunger front area. The first plunger front area is preferably smaller than the first pressure plate area. The first plunger front area further corresponds or substantially corresponds in size to the first chamber area. This means that the first plunger front area and the first chamber area preferably correspond or generally correspond in size and shape to each other such that the first plunger fits within the first chamber.

The second plunger has a free second front end oriented toward the material container. The second plunger may have a free second rear end oriented away from the material container. The second plunger at or adjacent the second front end preferably has a second plunger front surface laterally to the dispensing axis. The second plunger front surface has a second plunger front area. The second plunger front area is preferably smaller than the second pressure plate area. The second plunger front area further corresponds or substantially corresponds in size to the second chamber area. This means that the second plunger front area and the second chamber area preferably correspond or generally correspond in size and shape to each other such that the second plunger fits within the second chamber.

Therefore the first and second plungers may generally provide a change-over or reduction between the first and second pressure plate areas and the first and second chamber areas.

The first and second chamber areas are cross-sectional areas of the opening formed by the chambers. At least one of the first and second chamber areas is smaller than the smallest of the first and second pressure plate areas. Further the first chamber area may be smaller than the first pressure plate area, and the second chamber area may be smaller than the second pressure plate area.

In one embodiment the automatic mixing and dispensing device may be of a type suitable for mixing and dispensing a dental impression material. An automatic device for mixing and dispensing a dental impression material is typically provided with a relatively powerful drive to prepare relatively large amounts of impression material in a short time. The invention is advantageous because it preferably enables the use of such a device for mixing and dispensing a material that has a much higher viscosity than a dental impression material. Further the invention may allow using one automatic mixing and dispensing device for various types of dental materials, like impression materials, and filling materials for example. As another advantage the invention may enable automatic mixing of relatively high viscous dental materials, for example temporary crown and bridge materials or two component filling materials, which are typically otherwise mixed by hand or even cannot be easily mixed manually or by use of a static mixer. The invention thus overall may be advantageous in that it helps minimizing costs, time and efforts in the preparation of dental materials.

In one embodiment the first and second pressure plates are arranged side by side (preferably with the first and second pressure plate surfaces positioned substantially in a plane), and are synchronously movable parallel to the dispensing axis. Thus the pressure plates allow for extruding two components that are to be mixed at a generally uniform proportion relative to each other.

In another embodiment the material container has at least a first container outlet. Preferably at least the first material chamber at a front end of the first material chamber opens into the first container outlet. In addition the second material chamber may at a front end of the second material chamber also open into the first container outlet. The material container may however further have a second container outlet, and the second material chamber may at a front side of the second material chamber open into the second container outlet.

In the latter case the first material chamber at its front end may only open in the first container outlet, and the second material chamber at its front end may only open in the second container outlet.

In a further embodiment the material container comprises one of a foil bag and a cartridge. For example the material container may comprise a front to which a first and a second foil bag are attached, and the foil bags each may contain a component of the material. The foil bags may be compressed for dispensing the material from the material container. The material container may further comprise a front which carries first and second barrels that each contain a component of the material. The foil bags or the barrels of the cartridge preferably form the material chambers of the material container. Preferably the front and the container barrels are formed in one piece (for example monolithically with one another). Further the first, or the first and second outlets, are formed by a first container nozzle, or by a first container nozzle and a second container nozzle, respectively. The first and/or the second container nozzle may be formed in one piece (for example monolithically) with at least the front of the material container. The first and second container nozzles may in combination be configured for connecting with a mixer for mixing the components supplied from the first and second chambers.

In one embodiment the material container has a first and a second piston for closing first and second rear ends of the first and second material chambers, respectively. The first and second pistons are preferably movable in the first and second material chambers, respectively, substantially parallel to the chamber lengths (which corresponds to a direction generally parallel to the dispensing axis when the material container is placed in the reservoir of the mixing and dispensing device). Thus the first and second pistons may be used for advancing components stored in the first and second material chambers toward the first and second container outlets, respectively.

In a further embodiment the material container has a mounting piece for retaining the material container in a manually operable applicator device. Preferably the mounting piece is arranged adjacent a rear end of the material container which is preferably an end opposite of the first and second outlets. Such a mounting piece may comprise for example a circumferential or partly circumferential groove, or a circumferential or partly circumferential flange, or a combination of both. The skilled person will recognize different structures to allow the material container to be retained in an applicator device.

The mounting piece may particularly be adapted for use with at least one of an applicator available under the designation:

Garant™ Dispenser;
3M™ ESPE™ Clicker™;
3M™ ESPE™ Capsule Dispenser;
all being available from 3M ESPE AG, Germany.

In one embodiment the system further comprises an adaptor. The adaptor is preferably shaped to fit within the reservoir of the automatic mixing and dispensing device. Preferably the adaptor is shaped to fit in a predetermined position within the reservoir of the automatic mixing and dispensing device. Further the adaptor is may be adapted to position the material container within the reservoir, and to allow the first and second pressure plates of the automatic mixing and dispensing device to move relative to the material container. Thus the adaptor may enable the automatic mixing and dispensing device to extrude material from the material container. The adapter may for example have a rear end which is sized such that the first and second pressure plates can penetrate into the adapter. Further the adapter may have a size to provide a space between the rear end of the adaptor and the pressure plates, and that space is available for the pressure plates to move relative to the material container. Further the adaptor may have a front end comprising a receptacle for receiving at least part of the material container in the adaptor.

In one embodiment the first plunger is guided in the system, for example by the adaptor, for a movement generally parallel to the dispensing axis and may be restrained otherwise.

In a further embodiment the second plunger is guided in the system, for example by the adaptor, for a movement generally parallel to the dispensing axis and may be restrained otherwise.

In another embodiment the first plunger at or adjacent the first rear end has a first plunger rear surface laterally to the dispensing axis. The first plunger rear surface has a first plunger rear area which is preferably substantially within a range of the first plunger front area and the first pressure plate area. Further the second plunger at or adjacent the second rear end may have a second plunger rear surface laterally to the dispensing axis. The second plunger rear surface has a second plunger rear area which is substantially within a range of the third plunger area and the second pressure plate area.

In one embodiment the material container comprises one or both of the first and second plungers. The first and second plungers may further be accommodated in the adapter and the material container may be separable therefrom. Thus the material container may be replaced and the plungers may be reused for a new container. This may help minimizing waste and costs due to a replacement of the plungers along with empty material containers may be generally avoided. Further the first and second plungers may form a plunger unit in which the first and second plungers are formed in one piece (for example monolithically) or in which they are assembled from two or more separate pieces. The first and/or second plungers may further have a plunger length parallel to the dispensing axis, and that plunger length may be about half of the adaptor length.

In one embodiment the system, comprises a mixer which has a first and a second mixer inlet and a dispensing nozzle forming a mixer outlet. The first mixer inlet and the first container outlet are preferably adapted such that they can be interconnected with one another. Accordingly, the second mixer inlet and the second container outlet are preferably adapted such that they can be interconnected with one another.

Therefore a fluid communication between the first and second material chambers, on the one hand, and the mixer inlets, on the other hand, may be established. Such a mixer is preferably a dynamic mixer which is adapted for continuously receiving material from the material container through the first and second inlets, releasing the material at the dispensing nozzle and mixing the material as it flows from the mixer inlets toward the dispensing nozzle. The dynamic mixer preferably has a mixing rotor having a plurality of radially extending mixing paddles. Therefore the material components may be caused to flow substantially in a direction axially to the mixing rotor and the mixing paddles shear that material flow substantially transversely thereto to provide for mixing of the components during the flow along the mixing rotor. The system of the invention may however further contain a static mixer. The static mixer may have first and second mixer inlets and a dispensing nozzle forming a mixer outlet. The static mixer typically has a substantially non-rotating mixing helix which provides for dividing and merging a flow of the components through the mixer and thereby gradually causes the components to mix as they flow through the mixer.

In one embodiment the mixer has a minimized inner volume. The inner volume is preferably the free volume between the mixer inlets the dispensing nozzle. A particular embodiment comprises a dynamic mixer which has a mixing chamber volume of less than 10 ml, or in more particular less than 0.75 ml. Thus the amount of residual material in the mixer may be reduced.

In still another embodiment the system comprises an RFID receiver for communicating with an RFID data carrier for controlling a dispensing speed and/or a mixing speed of the automatic mixing and dispensing device.

A further aspect of the invention relates to a use of a device for automatic mixing and dispensing dental substance with a material container. The automatic mixing and dispensing device comprises a reservoir for receiving the dental substance, and a first and a second pressure plate which are movable parallel to a dispensing axis. The first pressure plate at or adjacent a free end has a first pressure plate surface laterally to the dispensing axis, and the first pressure plate surface has a first pressure plate area. Further the second pressure plate at or adjacent a free end has a second pressure plate surface laterally to the dispensing axis, and the second pressure plate surface has a second pressure plate area.

Further the material container of the use of the invention has a first and a second material chamber for containing components of a material. The first and second material chambers have first and second chamber cross-sections, respectively, each extending generally uniformly over a chamber length. Preferably the first and second chamber cross-sections are inner cross-sections of the chamber. The first and second chamber cross-sections have first and second chamber areas, respectively. At least one of the first and second chamber areas is smaller than the smallest of the first and second pressure plate areas.

In one embodiment of the use of the invention an adaptor is provided. The adaptor is preferably shaped to fit within the reservoir of the automatic mixing and dispensing device. Further the adaptor may be adapted to position the material container within the reservoir. The adaptor may further be adapted to allow the pressure plate of the automatic mixing and dispensing device to move relative to the material container for extruding material from the material container.

Another embodiment comprises the use of at least a first plunger which is movable for extruding material from the material container. The first plunger preferably has a free first front end oriented toward the material container and a free first rear end oriented away from the material container. The first plunger at or adjacent the first front end preferably has a first plunger front surface laterally to the dispensing axis. The first plunger front surface has a first plunger front area. The first plunger front area is preferably smaller than the first pressure plate area.

A further embodiment of the use of the invention comprises the use of a second plunger. The second plunger preferably has a free second front end oriented toward the material container and a free second rear end oriented away from the material container. The second plunger at or adjacent the second front end preferably has a second plunger front surface laterally to the dispensing axis. The second plunger front surface has a second plunger front area. The second plunger front area is preferably smaller than the second pressure plate area.

Further structures as defined for the system of the invention may be combined with the use of the invention to form embodiments of the use of the invention.

In still another aspect the invention relates to a use of an automatic mixing and dispensing system for dental impression materials in combination with a dental material which is not a dental impression material. In particular the automatic mixing and dispensing system for dental impression materials may be used in combination with at least one of a temporary crown and bridge material, for example one as available under the designation 3M™ ESPE™ Protemp™ from 3M ESPE AG, Germany, or a bulk curable two component composite filling material.

A further aspect of the invention relates to an adaptor which is adapted for fitting within a reservoir of an automatic mixing and dispensing device, and for receiving a material container. Such an adaptor is preferably particularly suitable for use in combination with the system of the invention. The adaptor is preferably adapted to cooperate with an automatic mixing and dispensing device for dental impression materials. Further the adaptor is adapted to receive a first and a second pressure plate of the automatic mixing and dispensing device.

Such first pressure plate at or adjacent a free end has a first pressure plate surface laterally to the dispensing axis, and the first pressure plate surface has a first pressure plate area. Further the second pressure plate adjacent a free end has a second pressure plate surface laterally to the dispensing axis, and the second pressure plate surface has a second pressure plate area.

The adaptor further has a receptacle which is adapted for receiving a material container having a first and a second material chamber for containing components of a material. Such first and second material chambers preferably extend at a generally uniform first and second chamber cross-section, respectively, over a chamber length. The first and the second chamber cross-section have first and second chamber areas. Further at least one of the first and second areas is smaller than the smallest of the first and second cross-sectional pressure plate areas. The adaptor further has at least a first plunger to compensate a difference in size between at least one of the first and second chamber areas and at least one of the first and second cross-sectional pressure plate areas.

In one embodiment the adaptor has a second plunger. In this embodiment the first plunger is preferably adapted to compensate a difference in size between the first chamber area and the first pressure plate area.

Further the second plunger is preferably adapted to compensate a difference in size between the second chamber area and the second pressure plate area.

In another embodiment the adapter is configured to use the movement of at least one of a first and a second pressure plate of an automatic mixing and dispensing device to advance a material in a material container that without the adaptor is incompatible for cooperation with the automatic mixing and dispensing device. In other words a dispensation of material stored in the material container by use of the automatic mixing and dispensing device may not be possible without the adaptor, unless the device, the container, or both are modified.

The adapter in one embodiment extends along a dispensing axis and is configured for receiving a material container by telescopically moving the adapter and the material container into one another in a direction parallel to the dispensing axis. The material container received in the adaptor is preferably restrained laterally to the dispensing axis. Further material container received in the adaptor is preferably further restrained in one direction parallel to the dispensing axis, but movable in the opposite direction. Thus the material container is preferably movable only in one direction parallel to the dispensing axis and restrained otherwise.

In another embodiment the receptacle of the adaptor has an inner cross-sectional area that is smaller than the smallest of the first and the second pressure plate areas. The inner cross-sectional area of the receptacle may further be smaller than a total of the first and the second pressure plate areas.

In one embodiment the adapter has a locking member for locking the material container in the adaptor. In a further embodiment the adaptor comprises a locking member for locking a mixer in the system or at the adaptor. The locking member may be further adapted to lock the mixer at the material container.

In another embodiment the adaptor further comprises a conduit for a drive shaft of the automatic mixing and dispensing device for driving a mixer. Thus the adapter may fit also in a reservoir through which a drive shaft of the mixing and dispensing device for driving a mixer extends.

Further the drive shaft may be used to drive a mixer for mixing a material from the material container. The adapter may further have an adaptor length, and the chamber length of the material container may be about half of the adaptor length.

In another embodiment the adaptor comprises an indicia area for providing information to a user. Such information may for example comprise instructions for use, information about a compatible material container, a compatible mixing and dispensing device, or any combination of those.

In another embodiment the adaptor has a machine readable code. For example the adaptor may comprise at least one of a RFID circuit, a bar code, and machine readable numbers and/or letters. The code may be recognizable by a reader in the automatic mixing and dispensing device and used to operate the device at certain operation parameters, like for example the speed at which the pressure plates are moved and/or the rotation speed of the mixer.

In a further embodiment the adaptor has a fill level indicator which is adapted to cooperate with the plunger and/or the material container to indicate a fill level of the material in the material container, for example when the material container is appropriately placed in the adaptor. In one embodiment the fill level indicator comprises a though-hole through a wall of the adaptor. Through the though-hole a structure may be observable which moves along with the fill level when material is dispensed from the material container. Further the material container may have a transparent window through which the fill level is visible. The through-hole of the adaptor may allow for the fill level in the material container to be directly observed from outside the adaptor. Further the through hole may be at least partially closed be a transparent window.

DETAILED DESCRIPTION OF THE INVENTION

Figure 1:
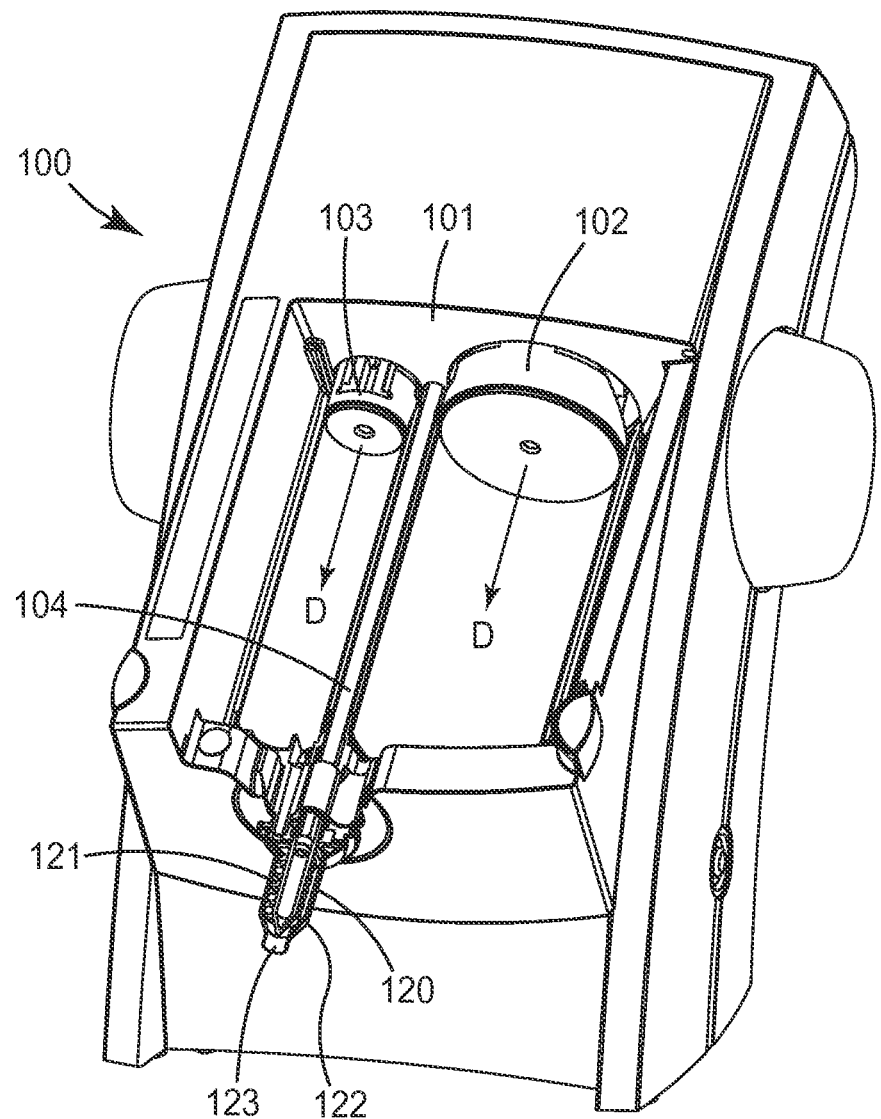
FIG. 1 is a perspective view of an automatic mixing and dispensing device according to an embodiment of the present invention.

FIG. 1 shows a device 100 for mixing and dispensing of dental materials. The device 100 has a reservoir 101 for receiving a dental substance. The dental substance may be provided in the form of two separately stored components in a cartridge (not shown). Typically such a cartridge has two generally parallel side by side compartments that are elongated in a longitudinal dimension and having a generally uniform cross-section along the longitudinal dimension. Pressure plates 102, 103 of the device 100 are typically sized to move into the compartments for advancing the substance in the longitudinal dimension from the compartments. In particular the pressure plates typically have a cross-section which substantially corresponds to the cross-section of the compartments. Further the pressure plates are spaced and guided for parallel movement at a certain distance from each other and the compartments are preferably spaced at substantially the same distance from each other. Such a distance is preferably measured between centers of the cross-sections, for example the centers of circular cross-sections of the pressure plates or the compartments.

The cartridge is further preferably shaped to fit with its outside inside the reservoir 101 of the device 100. In the example illustrated a mixer 120 for mixing the two components is arranged at the device 100. The mixer 120 has a mixing chamber formed between a rotatable mixing rotor 121 and a mixer housing 122. The mixing rotor 121 is connected to a drive shaft 104 of the device 100 so that the mixing rotor 121 can be rotated by the device 100. In (a not illustrated) use of the device 100 the mixer can be supplied with the components stored in the compartments. For this purpose the mixer is connectable to the compartments such that the individual components can flow into the mixing chamber where they can be mixed by help of rotating the mixing rotor 121. The mixture can exit through a mixer outlet 123 as further components are supplied into the mixer.

For obtaining an amount of mixed dental substance the components can be advanced toward the mixer 120 by the pressure plates 102, 103 of the device 100. The pressure plates 102, 103 are therefore movable in a dispensing axis which is indicated by the arrows "D" in the Figure.

The device 100 is motor driven such that the pressure plates are movable by motor power. Further the drive shaft 104 is motor driven so that the mixer can be operated by motor power.

The pressure plates and the mixing rotor can further preferably be driven simultaneously so that components can be continuously supplied to the mixer and mixed. Therefore the device 100 is adapted for automatically dispensing and mixing the dental substance. The skilled person will recognize that a motor as it can be used with the device illustrated may be an electric motor, for example an AC or a DC or a stepper motor, a hydraulic or pneumatic motor, or any other suitable motor.

The device shown may normally be used to mix and dispense a hardenable dental impression material, for example. The mixed material may be used to fill a dental tray which is then placed into a patient's mouth to take a dental impression. The mixer is replaceably attached at the device 100. Therefore when, for example, the mixed material hardens and thus blocks the mixer the used mixer may be replaced by an unused mixer for the next use of the device.

Figure 2:
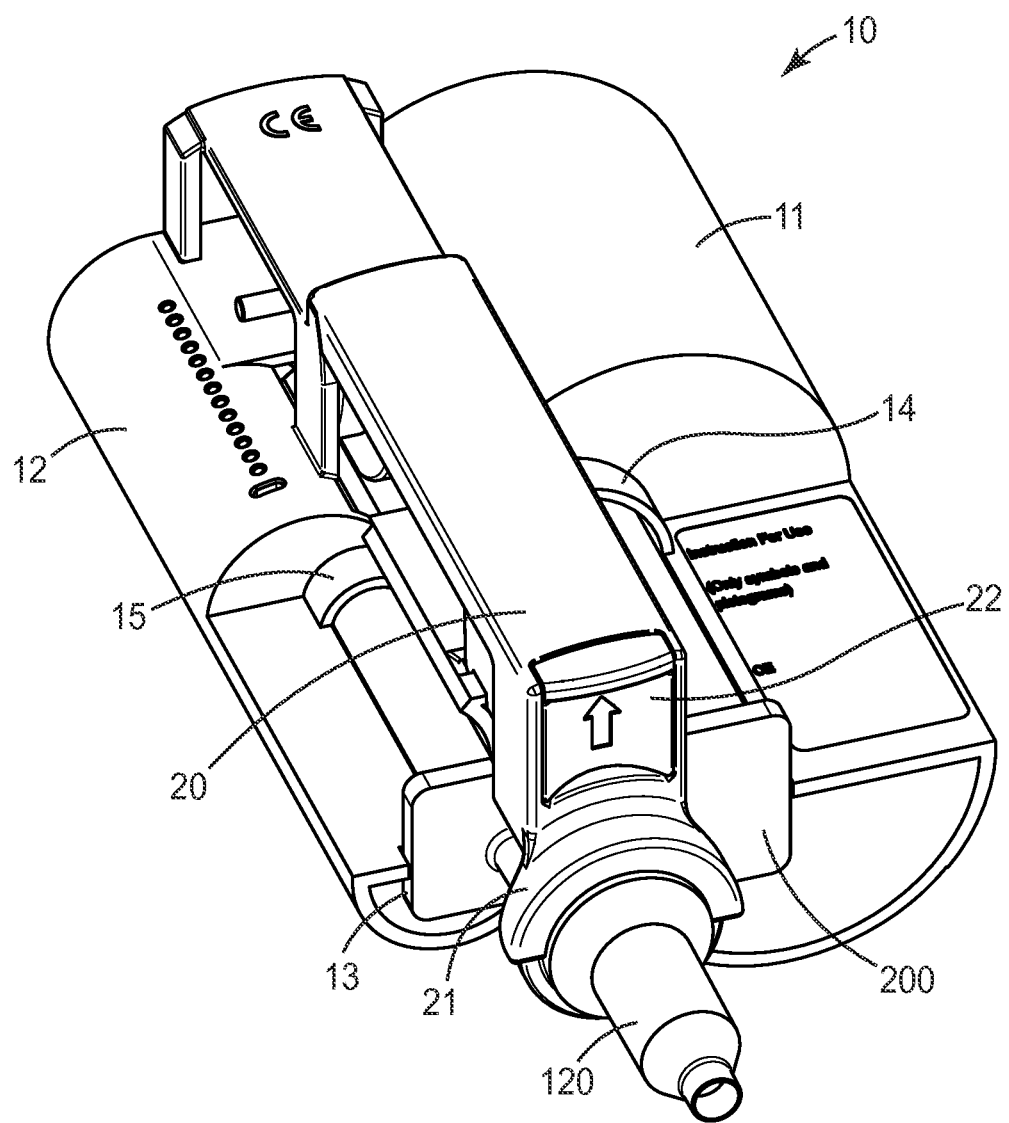
FIG. 2 is a perspective view of an adapter with a locking member in a first position according to an embodiment of the present invention.

FIG. 2 shows an adaptor 10 which is shaped to fit within a reservoir of an automatic mixing and dispensing device, for example one as shown in FIG. 1. The adaptor 10 has a first and a second adaptor tube 11, 12. The adaptor is outwardly shaped such that it can be inserted in the reservoir of the mixing and dispensing device in a predefined position, preferably in a unique predefined position. In the example the adaptor tubes 11, 12 are shaped and arranged relative to one another such that they substantially match with corresponding generally hollow cylindrical structures in the reservoir of the device. However the skilled person will recognize other suitable shapes of the adaptor or the adaptor tubes allowing likewise for appropriate positioning of the adaptor 10 in the reservoir of the device. Further the adaptor tubes 11, 12 may be replaced by other structures, like longitudinal or radial ribs or bars or any other structures that are suitable to appropriately position the adaptor 10 relative to the mixing and dispensing device.

The adaptor further has a receptacle 13 for receiving a material container 200 (described in more detail below). In the example the receptacle 13 is comprises third and fourth tubes 14, 15 which have a generally cylindrical inner shape. Thus the receptacle 13 is adapted to receive and position a material container that outwardly has two generally cylindrical barrels. The skilled person will recognize other shapes for a receptacle which can receive and position a material container having cylindrical barrels or another appropriate shape.

Further the adaptor has a locking member 20. The locking member 20 is movable between a first position (shown in the FIG. 2) and a second position (shown in FIG. 3). In the first position the locking member preferably locks the material container 200 with the adaptor 10. Thus the material container 200 may be prevented from falling out when the adaptor 10 is handled, for example when the adaptor 10 is inserted in the reservoir of the mixing and dispensing device. Further the locking member 20 in the first position may lock a mixer 120 (if present as shown) relative to the material container 200 and relative to the adapter 10. For locking the mixer 120 the locking member has a locking arm 21. The locking member 20 is preferably retainable in the first position, for example by a retention mechanism (not visible in this view). Therefore the locking member 20 may in the first position be fixedly retained and thus usable as a handle for carrying the adapter 10. The adaptor has a release actuator 22 which allows the retention to be suspended such that the locking member can be moved toward the second position. In the example the release actuator 22 is arranged at the locking member. This preferably provides for a relatively convenient operation of the release actuator 22, for example when the adaptor 10 is grasped at the locking member 20 by a user.

Figure 3:
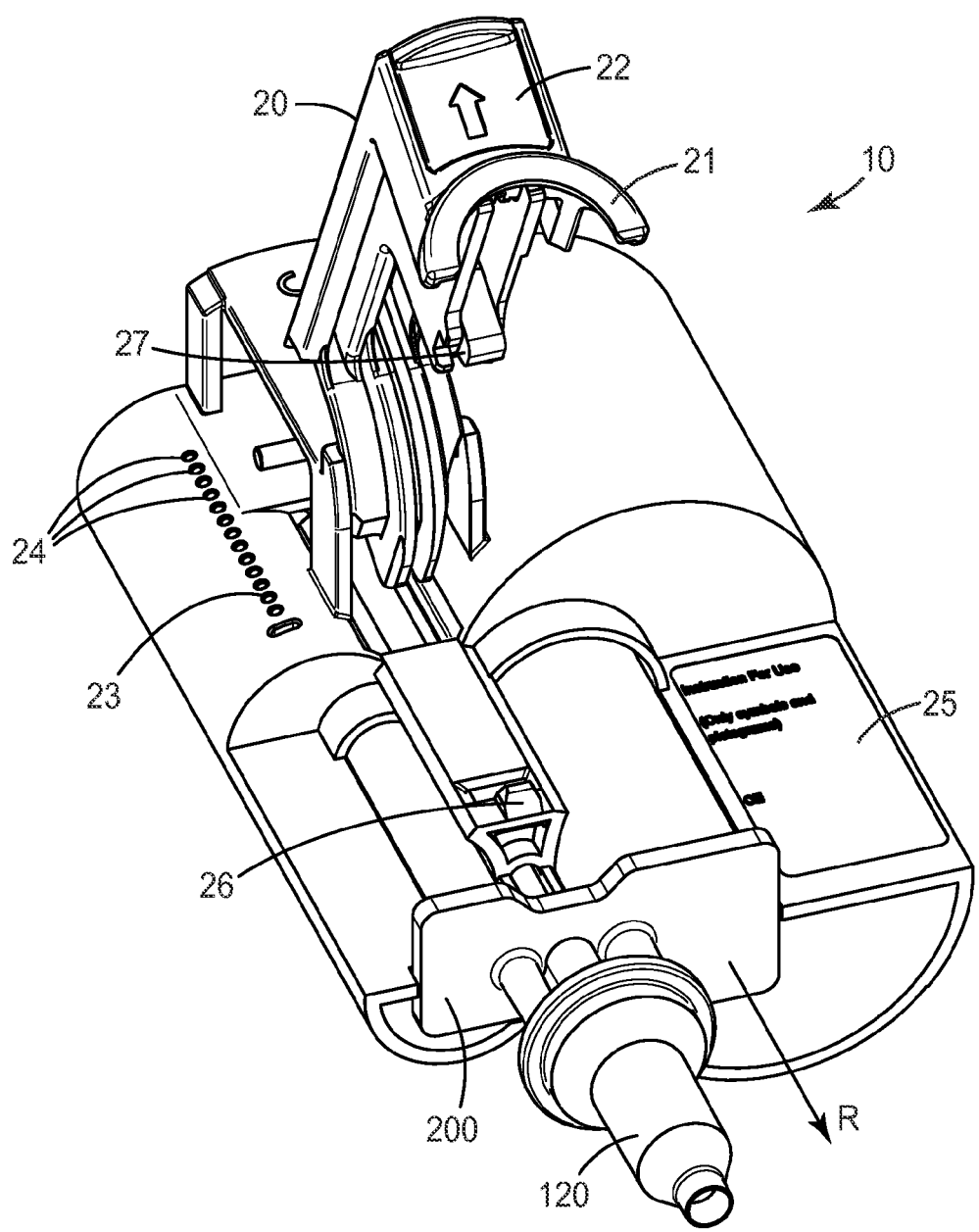
FIG. 3 is a perspective view of an adapter with a locking member in a second position according to an embodiment of the present invention.

FIG. 3 shows the adaptor 10 with the locking member 20 placed in the second position. In the second position the material container is unlocked. Thus the material container 200 is removable from the adaptor 10. In the Figure the direction in which the material container is removable is indicated by the arrow "R". Further the locking arm 21 in the second position also unlocks or disengages the mixer 120. The mixer 120 and the material container 200 are attached, for example plugged, to one another. Thus the mixer 120 is in fluid communication with the material container 200 and retained on the material container 200. Therefore the mixer 120 is prevented from falling off when unlocked and may be conveniently pulled off by a user when desired, for example in the direction R.

The retention mechanism for retaining the locking member 20 with the adaptor 10 comprises mutually engageable detents 26, 27. The first detent 26 is arranged at the adaptor, and the second detent 27 is arranged at the locking member 20. The second detent 27 is preferably movable by the release actuator 22 for disengaging the detents 26, 27. Further the second detent 27 is preferably urged, for example by spring load, in a direction opposite of the direction it is movable by the release actuator 22. Thus the locking mechanism may by default be maintained in an engaged position.

This may also allow the locking member to be just pushed from the second position toward the first position until the detents 26, 27 automatically snap into engagement with one another. Further the locking member 20 may be urged toward the second position, for example by spring load, such that the locking member 20, when unlocked, automatically moves toward the second position where it is maintained. This may facilitate replacement of the material container and/or the mixer because the locking member is maintained away from locking the material container and/or the mixer.

The adaptor 10 further has a fill level indicator 23. The fill level indicator 23 preferably indicates the amount of material contained in the material container. In the example the fill level indicator 23 comprises a plurality of linearly arranged through holes 24 through a wall in the adaptor, behind which the position of an indicator structure can be observed. Such an indicator structure may for example be moved along with extruding material from the material container 200, so that the position of it may be recognized as the fill level of the container.

Further the adapter may have a generally flat indicia area 25, for example comprising instructions for use of the adaptor.

Figure 4:
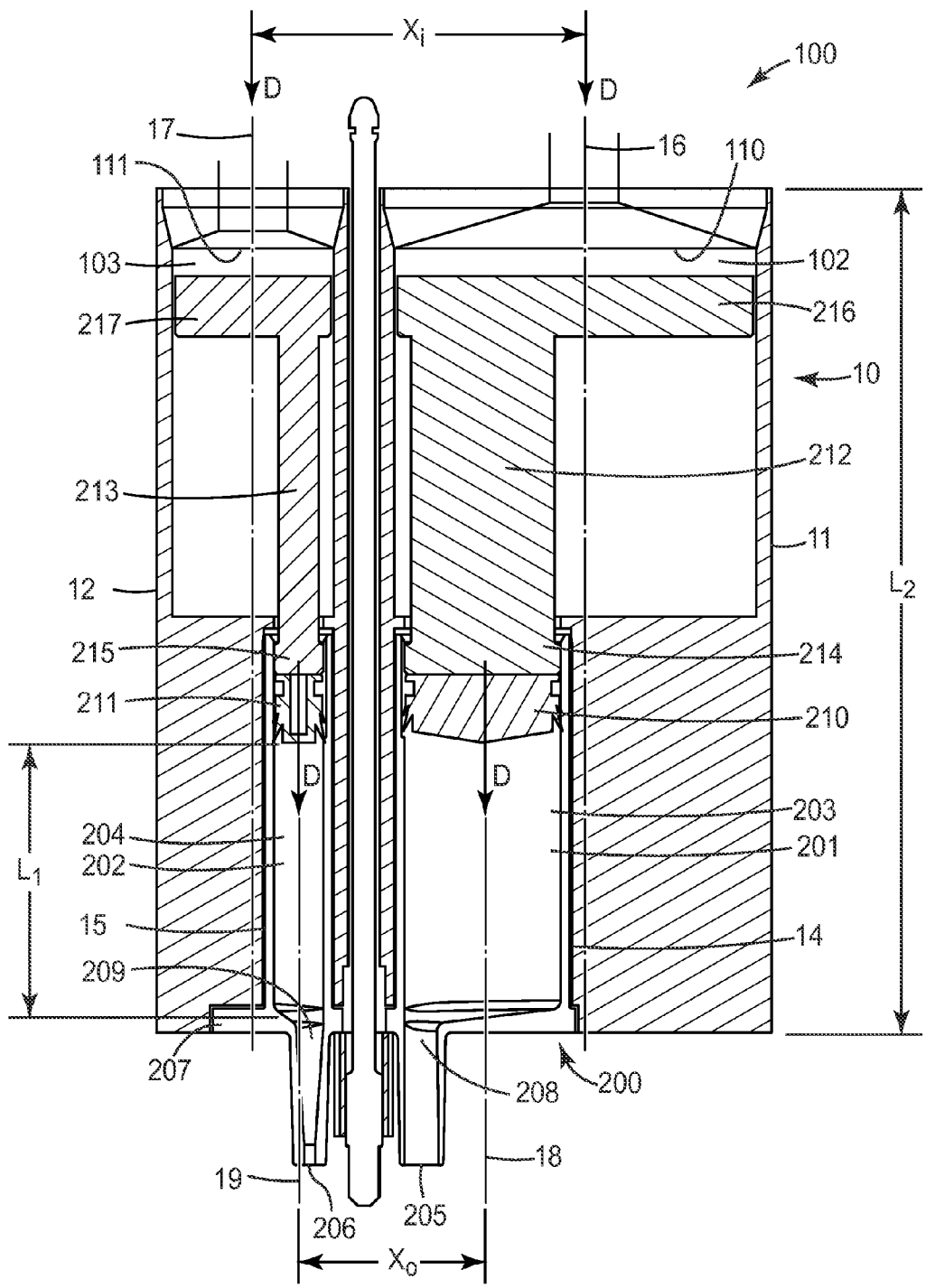
FIG. 4 is a cross-sectional view of at least part of a system including an adapter according to an embodiment of the present invention.

FIG. 4 is a cross-sectional view of the adaptor 10, inserted in a mixing and dispensing device 100. For ease of description, only the first and second pressure plates 102, 103 of the mixing and dispensing device 100 are illustrated. The arrows "D" again indicate the direction in which the pressure plates 102, 103 can be moved for advancing a substance or material for dispensation. The first and second pressure plates have a first and a second pressure plate surface 110, 111, respectively, laterally to the dispensing axis D. The first and second pressure plate surfaces define first and second pressure plate areas. In the example the adaptor 10 is configured such that the first and second pressure plates 102, 103 can move in the dispensing axis into a rear end of the adaptor 10. The adaptor 10 at a front end accommodates a material container 200. The material container 200 has a first and a second barrel 201, 202. The first barrel 201 forms a first material chamber 203, and the second barrel 202 forms a second material chamber 204. Each of the first and second material chambers 203, 204 extend along a dispensing axis D'. The dispensing axis D' in the example is a direction in which material can be moved in the barrels for extruding material from the material container.

In the example the adaptor 10 is configured for positioning the material container 200 such that the dispensing axis D' of the material container 200 generally corresponds to (is generally parallel to) the dispensing axis D of the mixing and dispensing device 100. The first and second material chambers 203, 204 each have a generally uniform cross-section along a certain chamber length L1 in a dimension parallel to the dispensing axis D'. Preferably the first material chamber 203 has a first cross-section defining a first (cross-sectional) area which is smaller than the first pressure plate area of the first pressure plate 102, and the second material chamber 204 has a second cross-section defining a second (cross-sectional) area which is smaller than the second pressure plate area of the second pressure plate 103. Thus the adaptor 10 allows for using a mixing and dispensing device having pressure plates defining a certain cross-sectional area with a material container having chambers defining a smaller cross-sectional area. Therefore although the pressure plates of the mixing and dispensing device do not fit in the material chambers of the material container for extruding material from the container the adaptor enables the mixing and dispensing device for extruding material from the material container.

The adaptor 10 in the example has a first and a second plunger 212, 213. The first plunger 212 has a first plunger front end 214 and a first plunger rear end 216, whereas the second plunger 213 has a second plunger front end 215, and a second plunger rear end 217. In the example the first plunger front end 214 is smaller than the first plunger rear end 216. Further in the example the second plunger front end 215 is smaller than the second plunger rear end 217. Thus the plungers 212, 213 can be moved by the pressure plates 102, 103, respectively, but can also advance material contained in the first and second material chambers 203, 204, respectively. The plungers 212, 213 may be part of the adapter 10. Therefore the plungers 212, 213 may not need to be replaced together with the material container, for example for exchanging an empty material container by a full one. However the plungers may further form part of the material container.

In the example the material container 200 has a first and a second piston 210, 211 which are movably arranged within the first and second material chambers 203, 204, respectively. The pistons 210, 211 are movable within the material chambers 203, 204 in the dispensing axis D' for dispensation of material from the material container 200. The pistons 210, 211 can be moved by the plungers 212, 213, respectively. However the skilled person will recognize that the pistons may also be replaced by the plungers. In this case the plungers may not be part of the adaptor, but part of the material container. The adaptor is preferably further adapted to guide the plungers 212, 213 in the dispensing axis D of the mixing and dispensing device 100. Therefore the plungers 212, 213 may be maintained in a parallel relationship to the dispensing axis D and/or D' during dispensation of material from the material container 200.

Further the material container 200 has a first and a second container nozzle 205, 206 forming first and second outlets 208, 209, respectively. The first and second material chambers 203, 204 open into the first and second outlets 208, 209, respectively. The container 200 has a front 207. The front 207 may connect the first and second barrels 201, 202 as illustrated, but may further be split for removably connecting the first and the second barrels. The front 207 further carries the first and second container nozzles 205, 206, and closes the first and second chambers 203, 204 at a front end, but provide first and second outlets 208, 209 into the first and second nozzles 205, 206, respectively.

The material container front 207 protrudes from the barrels 201, 202 laterally to the dispensing axis D'. Thus the front 207 may form a stop for retaining the material container 200 in a certain position in the adaptor 10.

The first and second tubes 11, 12 of the adaptor 10 have first and second center axes 16, 17, respectively. A center axis is preferably defined by the center of a cross-section of a tube and a longitudinal dimension in which the cross-section extends generally uniformly. The first and second tubes 11, 12 are preferably arranged relative to one another such that their first and second center axes 16, 17 are generally parallel and spaced from one another at an input distance Xi. The input distance Xi preferably corresponds to a distance of the pressure plates 102, 103 of the mixing and dispensing device relative to one another. For example the pressure plates may be generally circular in a dimension laterally to the dispensing axis and the input distance may generally correspond to the distance of the centers of such circular pressure plates. Further the third and fourth tubes 14, 15 have third and fourth center axes 18, 19. The third and fourth tubes 14, 15 are arranged with their third and fourth center axes 18, 19 spaced at an output distance Xo. The output distance is smaller than the input distance in the example. Therefore the adaptor allows for using a material container in the mixing and dispensing device although the material container has a barrel distance that is different from the pressure plate distance of the device. Accordingly the material container may have generally cylindrical side by side barrels which cylinder axes are spaced at an output distance Xo. In the example the first center axis 16 and the third center axis 18 are parallel offset relative to one another. Further the second center axis 17 and the fourth center axis 19 are parallel offset relative to one another.

Although the example refers to generally cylindrical structures the skilled person will recognize other shapes, like oval or D-shaped or any other suitable shape. For example a chamber of a material container may generally have a certain uniform cross-section over a certain chamber length. Such a chamber may have a longitudinal axis defined by the center of the chamber cross-section in a direction of the chamber length. The adaptor may generally allow for using a material container in which the longitudinal material chamber axes are spaced at a certain output distance with an automatic mixing and dispensing device having differently spaced pressure plates.

Further the adaptor 10 has a certain adaptor length L2. The chamber length L1 of the material container 200 is preferably less than about 50% of the adaptor length L2. Therefore the adaptor and the material container fit within an existing mixing and dispensing device, and avoid extending the overall size of the device when combined with the adaptor and the material container.

Figure 5A:
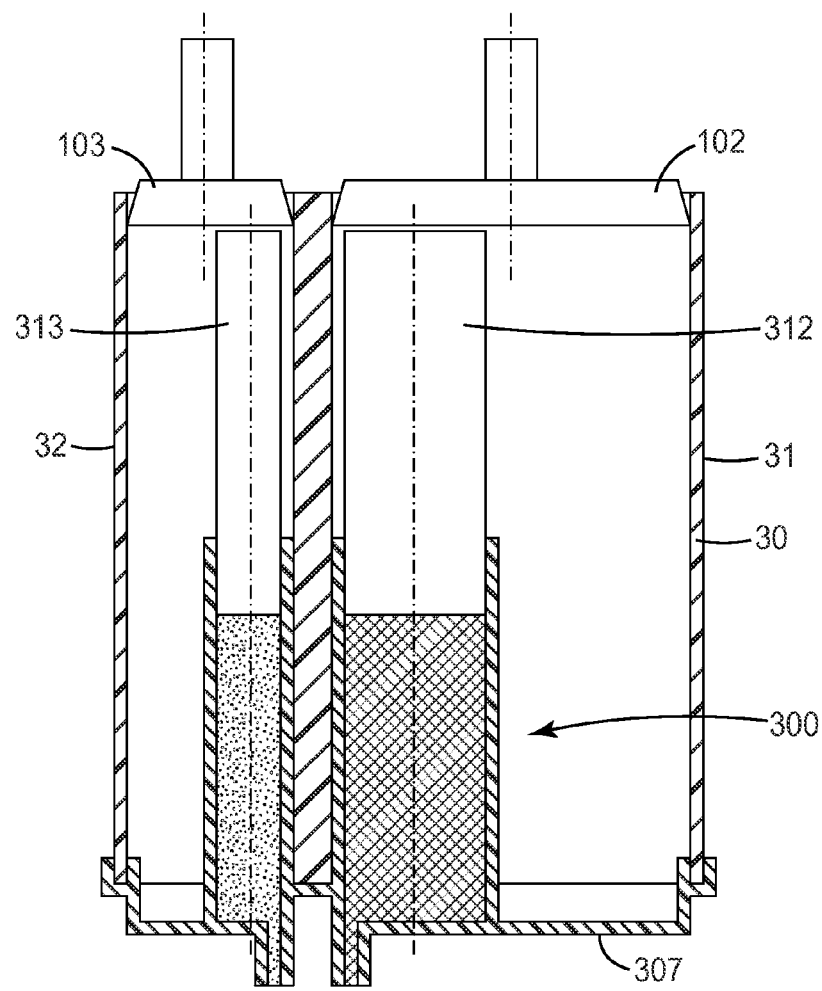
FIG. 5a, 5b, 5c are cross-sectional views of at least part of a system including an adapter according to another embodiment of the present invention.

FIG. 5a shows an adaptor 30 which accommodates a material container 300. The adaptor 30 has two generally parallel and generally cylindrical tubes 31, 32 which are open at both ends. The tubes 31, 32 are sized such that they can receive the pressure plates 102, 103 of the automatic mixing and dispensing device 10 (not shown in its entirety) at a rear end. Further the material container 300 is shaped for being received in the adaptor 30. In particular the material container 300 has a front 307 which can be mated with a front end of the adaptor 30. The adaptor 30 thus may be used to receive material containers of a different size, shape and/or configuration, and the corresponding different material containers may have a uniform front portion fitting with the front end of the adaptor 30. In the example the adaptor 30 has tubes having a generally uniform cross-section (diameters) over the entire adaptor length. Thus the adaptor 30 may be used likewise with foil bag material containers (not shown) which may be directly inserted in the tubes 31, 32 of the adaptor 30. Such foil bag material containers may have outer cross-sections that are similar to the respective inner cross-sections of the tubes. Thus the inner walls of the tubes support the outer walls of the foil bags during extrusion of material from pressurizing the foil bags by the pressure plates.

Figures 5B, 5C:
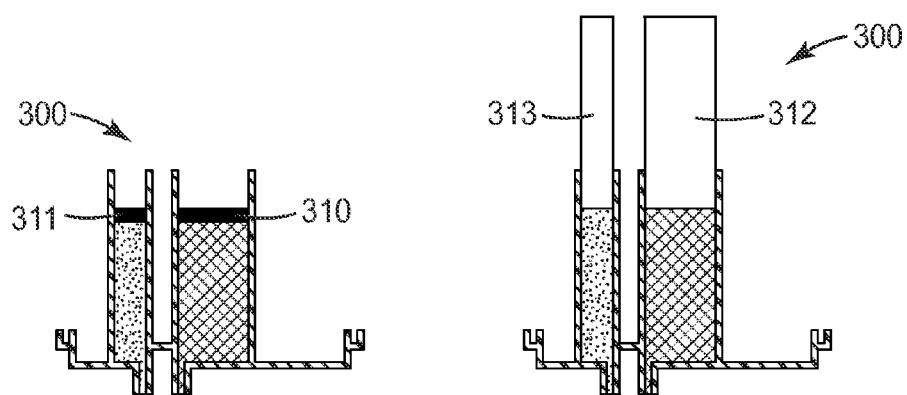

As illustrated in FIGS. 5b and 5c the material container 300 may comprise pistons 311, 310 and/or plungers 312, 313. The plungers 312, 313 may be moved by the pressure plates 102, 103 for extruding material from the material container 300.

Figure 6A:
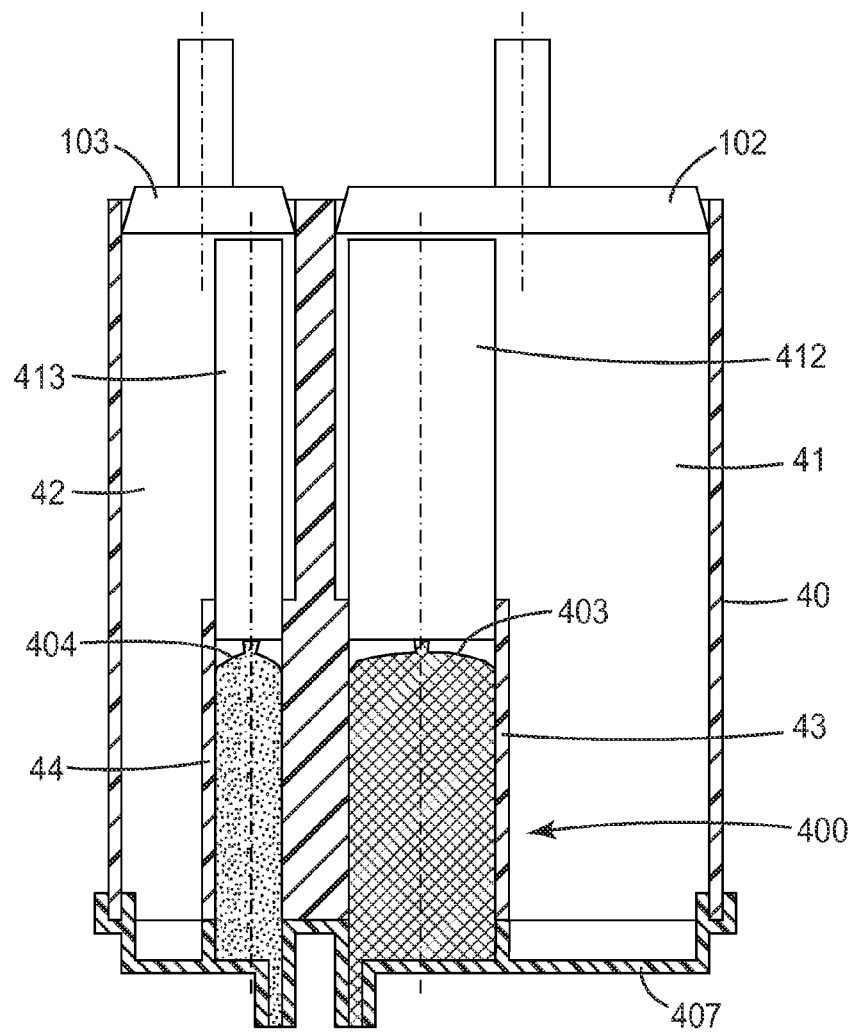
FIG. 6a, 6b are cross-sectional views of at least part of a system including an adapter according to a further embodiment of the present invention.

FIG. 6a shows an adaptor 40 with an alternative material container 400. The adaptor 40 comprises first and second tubes 41, 42 and third and fourth tubes 43, 44. The third and fourth tubes 43, 44 form a receptacle for first and second foil bags 403, 404 of the material container 400. The first tube 41 has a first inside cross-sectional area and the third tube 43 has a third cross-sectional area that is smaller than the first cross-sectional area. Further the second tube 42 has a second inside cross-sectional area and the fourth tube 44 has a fourth cross-sectional area that is smaller than the second cross-sectional area. Further the foil bags 403, 404 preferably have outer cross-sections which substantially correspond to the respective third and fourth inner cross-sections. Thus the foil bags may be supported by the third and fourth tubes during extrusion of material from pressurizing the foil bags by the pressure plates 102, 103. The third and fourth tubes 43, 44 may be reinforced, for example by webs extending between an outside of the third and fourth tubes 43, 44 and an inside of the first and second tubes 41, 42, respectively. The space between the outside of the third and fourth tubes 43, 44 and the inside of the first and second tubes 41, 42 may further be filled to support the third and fourth tubes 43, 44, for example by a foam. Therefore the third and fourth tubes 43, 44 may have a sufficient mechanical stability to restrain the foil bags, when pressurized for dispensing material.

Figure 6B:
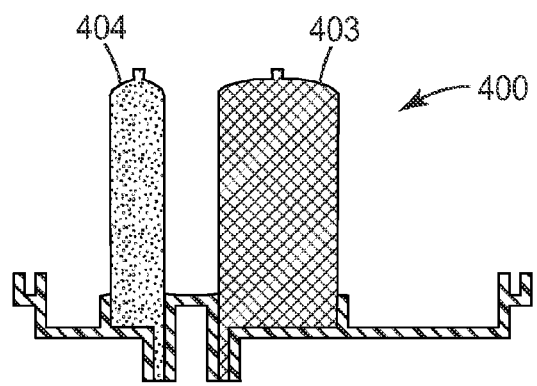

The third and fourth tubes may alternatively form part of the material container, instead forming part of the adaptor as described above. In this example the third and fourth tubes may surround the foil bags over substantially the full length (in FIG. 6b along a direction between the bottom and top of the page) and not as illustrated in FIG. 6b just over a part of the length.

The foil bags 403, 404 are attached to a, preferably common, front 407 of the material container 400. Thus the material container 400 including the foil bags 403, 404 can be removably received in the adaptor 40. FIG. 6b illustrates the material container 400 apart from the adaptor 40. The foil bags may help minimizing waste. This is because the plungers 412, 413 may be reusable because they may be normally prevented from contacting the material in the container. Further the amount of material which the container is formed of may be minimized by use of a relatively thin foil.

Figure 7:
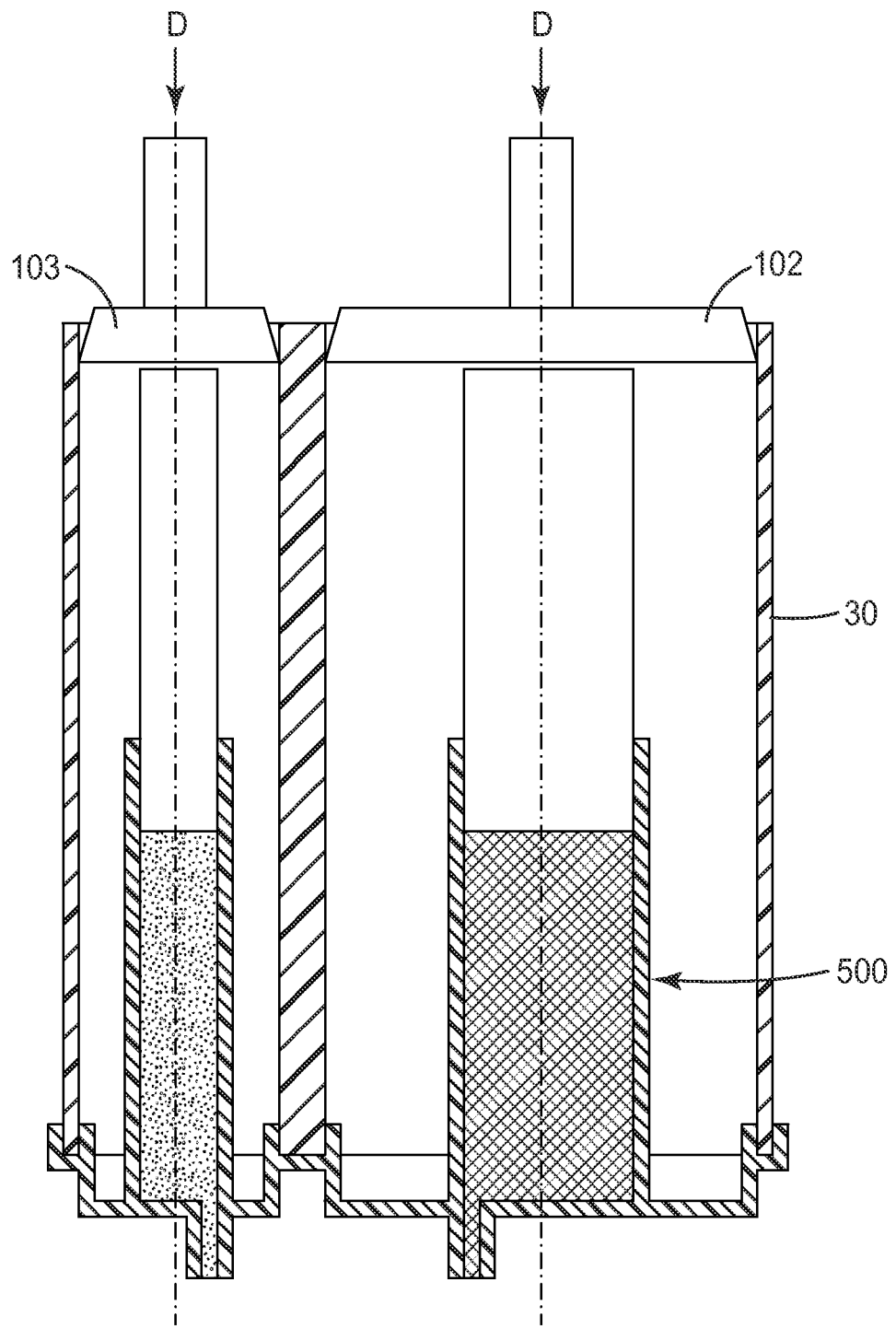
FIG. 7 is a cross-sectional view of at least part of a system including an adapter according to still another embodiment of the present invention.

FIG. 7 shows the adaptor 30 which corresponds to the adaptor shown in FIG. 5, but with the center axes of the material chambers of the material container 500 aligned with the center axes of the pressure plates 102, 103. Thus forces lateral to the dispensing axis D resulting from forcing the pressure plates against the material container may be minimized.

Figure 8:
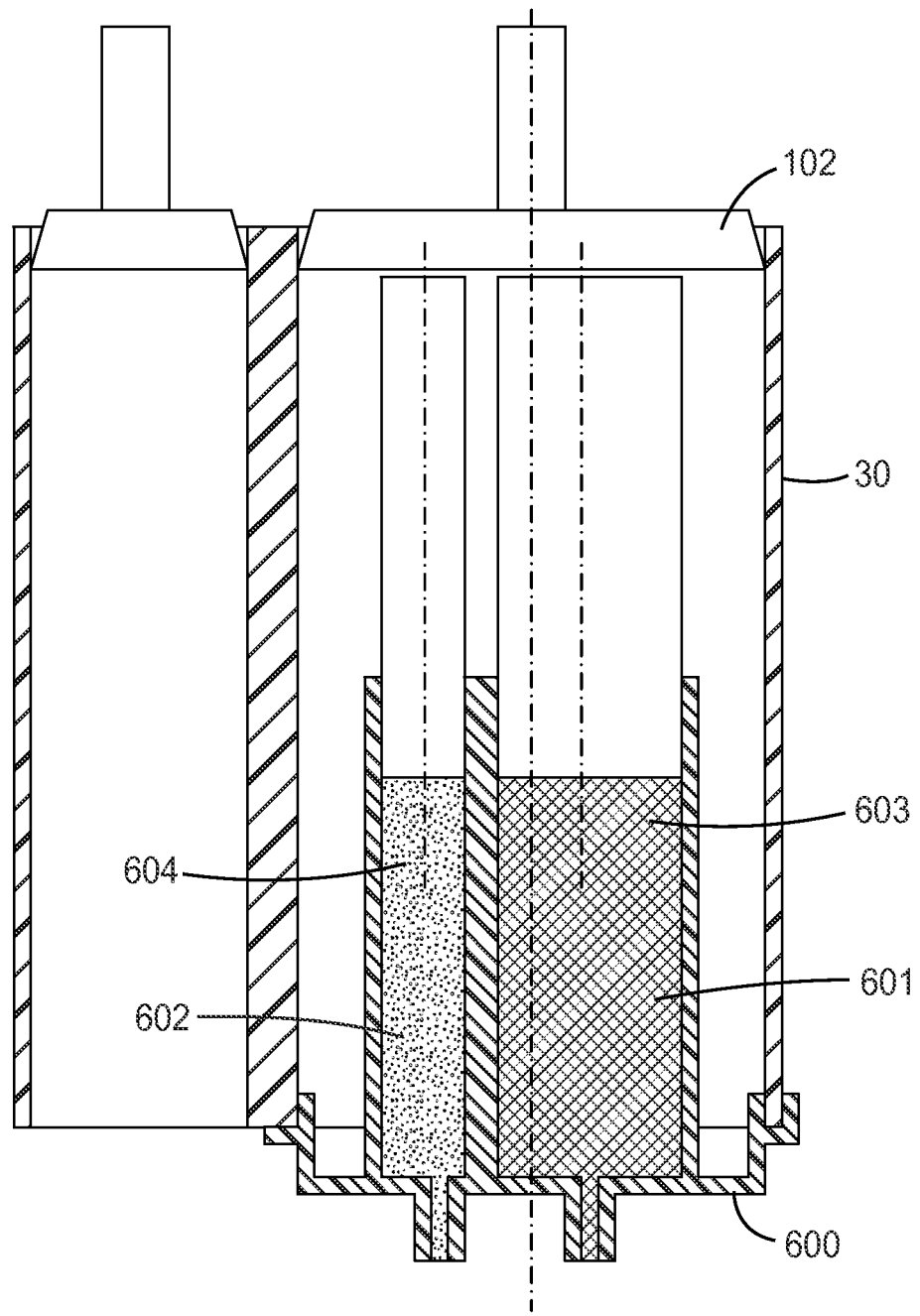
FIG. 8 is a cross-sectional view of at least part of a system including an adapter according to an alternative embodiment of the present invention.

FIG. 8 shows the same adaptor 30 which accommodates a material container 600 in one of the two tubes of the adaptor 30. The material container 600 has two side by side barrels 601, 602 forming two material chambers 603, 604. The cross-sections of the material chambers together form an overall cross-sectional area (in the example composed of two circular cross-sectional areas) which center axis substantially coincides with a center axis of the pressure plate 102.

Figure 9:
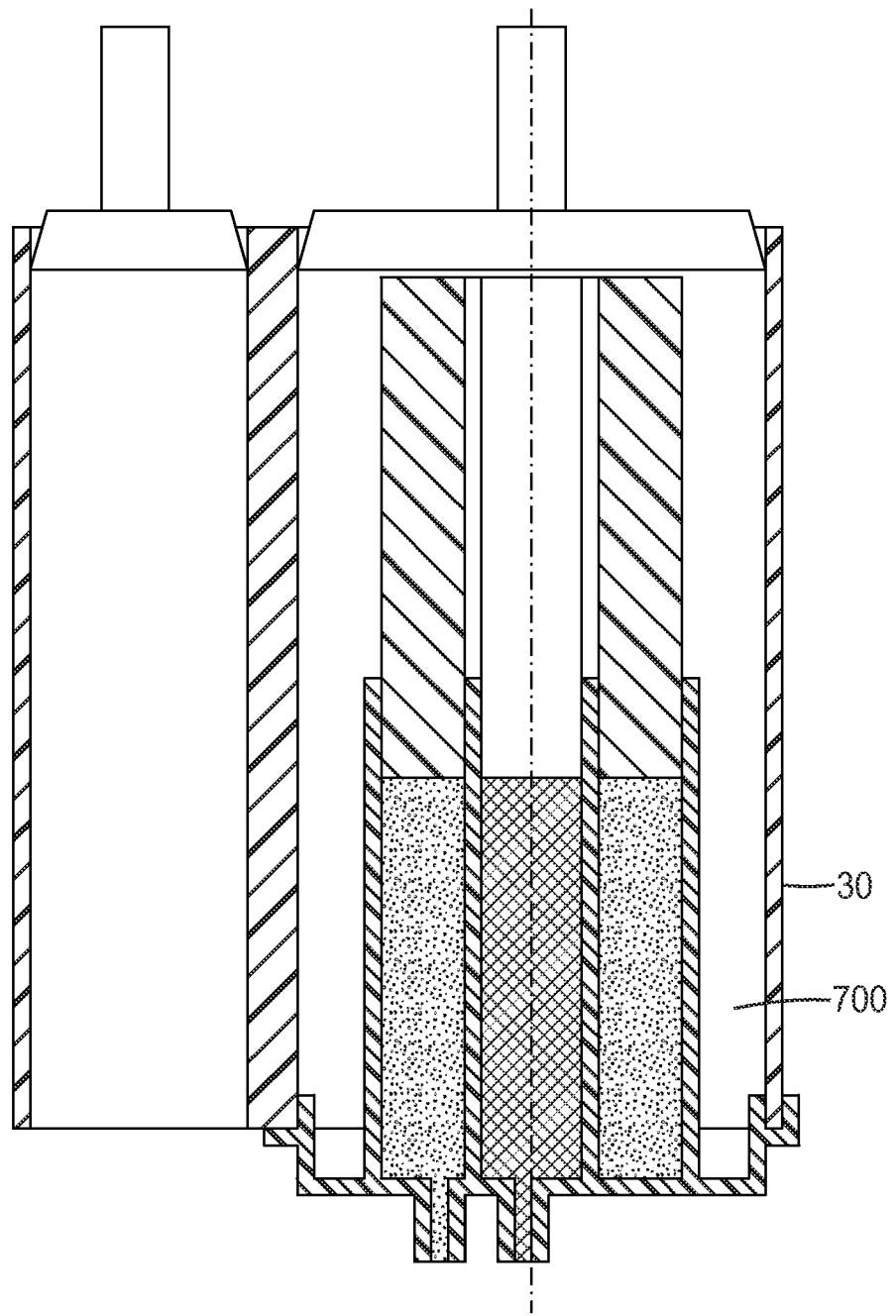
FIG. 9 is a cross-sectional view of at least part of a system including an adapter according to another alternative embodiment of the present invention.

FIG. 9 illustrates the adaptor 30 with a material container 700 having two concentric material chambers.

The skilled person will recognize other configurations of the material container. For example the configuration shown in FIGS. 7, 8, 9 may use compressible foil bags instead of barrels from which material is extruded. Further instead the material container may have three or more barrels for containing more than two components of a material, for example.

The invention claimed is:
1. A system comprising:
   an automatic mixing and dispensing device for a dental substance, and a material container;
   the automatic mixing and dispensing device comprising:
      a reservoir for receiving the dental substance and the material container;

a first pressure plate and a second pressure plate which are movable through the reservoir parallel to a dispensing axis;

the first pressure plate adjacent a free end having a first pressure plate surface located laterally to the dispensing axis, the first pressure plate surface having a first pressure plate area, and the second pressure plate adjacent a free end having a second pressure plate surface located laterally to the dispensing axis, the second pressure plate surface having a second pressure plate area;

a first plunger and a second plunger which are movable generally parallel to the dispensing axis for extruding material from the material container in the reservoir;

the material container having a first and a second material chamber for containing components of a material, the first and second material chambers having a first and a second chamber cross-section, respectively, each extending generally uniformly over a chamber length, the first and second chamber cross-sections having a first and second chamber area; and wherein the first plunger has a free first front end oriented toward the material container, and the second plunger has a free second front end oriented toward the material container; and wherein the first plunger adjacent the first front end has a first plunger front surface laterally to the dispensing axis, and the first plunger front surface has a first plunger front area which corresponds to the first chamber area; and wherein the second plunger adjacent the second front end has a second plunger front surface laterally to the dispensing axis, and the second plunger front surface has a second plunger front area which corresponds to the second chamber area;

wherein at least one of the first and second chamber areas is smaller than the smallest of the first and second pressure plate areas; and wherein the first and second plungers are insertable within the first and second material chambers to extrude material therefrom.

2. The system of claim 1, wherein the material container has at least a first container outlet, into which the first material chamber opens at a front end of the first material chamber, and optionally a second container outlet, into which the second material chamber opens at a front end of the second material chamber.

3. The system of claim 2, comprising a mixer which has first and second mixer inlets and a dispensing nozzle, the first and second mixer inlets and the first and second container outlets, respectively, being adapted such that they can be interconnected with one another to establish a fluid communication between the first and second material chambers and the mixer inlets.

4. The system of claim 1, in which the material container comprises a foil bag.

5. The system of claim 4, in which the material container has a first and a second piston for closing first and second rear ends of the first and second material chambers, respectively, and wherein the first and second pistons are movable in the first and second material chambers, respectively, parallel to the chamber length.

6. The system of claim 1, in which the material container has a mounting piece for retaining the material container in an applicator device.

7. The system of claim 1, further comprising an adaptor being shaped to fit within the reservoir of the automatic mixing and dispensing device;

the adaptor being adapted to position the material container within the reservoir; and to allow the first and second pressure plates of the automatic mixing and dispensing device to move relative to the material container.

8. The system of claim 7, in which the adaptor comprises a locking member for locking a mixer in the system.

9. The system of claim 7, comprising a conduit for a drive shaft of the automatic mixing and dispensing device for driving a mixer.

10. The system of claim 1, where the first plunger has a first front end oriented toward the material container and a first rear end oriented away from the material container;

the first plunger at the first front end having a first plunger surface laterally to the dispensing axis, the first plunger surface having a first plunger area;

wherein the first plunger area is smaller than the first pressure plate area.

11. The system of claim 10, further having a second plunger having a second front end oriented toward the material container and a second rear end oriented away from the material container, wherein the second plunger at the first front end having a second plunger surface laterally to the dispensing axis, the second plunger surface having a second plunger area, and wherein the second plunger area is smaller than the second pressure plate area.

12. The system of claim 1 in combination with a dental material selected from among a temporary crown and bridge material, and a composite filling material.

13. A device for automatic mixing and dispensing a dental substance with a material container, comprising:

the automatic mixing and dispensing device comprising:

a reservoir for receiving the dental substance and the material container;

a first pressure plate and a second pressure plate which are movable through the reservoir parallel to a dispensing axis;

the first pressure plate adjacent a free end having a first pressure plate surface laterally to the dispensing axis, the first pressure plate surface having a first pressure plate area, and the second pressure plate adjacent a free end having a second pressure plate surface laterally to the dispensing axis, the second pressure plate surface having a second pressure plate area;

the material container having a first and a second material chamber for containing components of a material, the first and second material chambers extending over a chamber length at a generally uniform chamber cross-section; and wherein at least one of the first and second chamber areas is smaller than the smallest of the first and second pressure plate areas; and a first plunger and a second plunger which are movable generally parallel to the dispensing axis for extruding material from the material container in the reservoir, wherein the first plunger and the second plunger are insertable within the first and second material chambers to extrude material therefrom.

14. An adaptor which is adapted for fitting within a reservoir of an automatic mixing and dispensing device and for receiving a material container, wherein the adaptor is further adapted to receive a first and a second pressure plate of the automatic mixing and dispensing device, wherein the first and second pressure plates having a first and a second pressure plate surfaces, respectively, the first and second pressure plate surfaces having first and second areas, respectively, the adaptor further having a receptacle which is adapted for receiving a material container having a first and a second material chamber for containing components of a material, the first and second material chambers extending over a chamber length at a generally uniform chamber cross-section, the first and second chamber cross-sections having a first and a second chamber area;

wherein at least one of the first and second chamber areas is smaller than the smallest of the first and second pressure plate areas; and wherein the adaptor further has a first plunger and a second plunger, wherein the first plunger is sized to compensate a difference in size between the first chamber area and the first pressure plate area, and wherein the second plunger is sized to compensate a difference in size between the second chamber area and the second pressure plate area; and wherein the first and second plungers are insertable within the first and second material chambers to extrude material therefrom.

* * * * *